United States Patent [19]

Nasu

[11] Patent Number: 5,425,708
[45] Date of Patent: Jun. 20, 1995

[54] CATHETER WITH AN AORTA-OCCLUDING BALLOON

[75] Inventor: Norio Nasu, Kagawa, Japan

[73] Assignee: Nissho Corporation, Osaka, Japan

[21] Appl. No.: 989,137

[22] Filed: Dec. 11, 1992

[30] Foreign Application Priority Data

Dec. 13, 1991 [JP] Japan .................. 3-352286

[51] Int. Cl.$^6$ ............................................. A61M 29/00
[52] U.S. Cl. ................................................... 604/96
[58] Field of Search ............... 604/96, 101, 284, 4, 604/27, 43, 53, 264, 280; 606/192–195

[56] References Cited

U.S. PATENT DOCUMENTS

| | | | |
|---|---|---|---|
| H85 | 7/1986 | Shortsleeve | 604/284 |
| 2,854,982 | 10/1958 | Pagano | 604/101 |
| 3,042,021 | 7/1962 | Read | 604/284 |
| 3,394,705 | 7/1968 | Abramson | 604/96 |
| 4,119,100 | 10/1978 | Niekett | 604/96 |
| 4,211,233 | 7/1980 | Lin | 604/96 |
| 4,573,966 | 3/1986 | Weiki et al. | 604/101 |
| 4,630,609 | 12/1986 | Chin | 606/194 |
| 4,712,551 | 12/1987 | Rayhanabod | 604/96 |
| 4,734,094 | 3/1988 | Jacob et al. | 604/284 |
| 4,771,776 | 9/1988 | Powell et al. | 604/96 |
| 4,983,166 | 1/1991 | Yamawaki | 604/96 |
| 5,044,369 | 9/1991 | Sahota | 604/96 |
| 5,116,305 | 5/1992 | Milder et al. | 604/96 |
| 5,219,355 | 6/1993 | Pakodi et al. | 606/191 |
| 5,261,875 | 11/1993 | Spears | 606/194 |

OTHER PUBLICATIONS

USCI Positrol II & NY Core Cardiovascular Catheters.

*Primary Examiner*—C. Fred Rosenbaum
*Assistant Examiner*—Manuel Mendez
*Attorney, Agent, or Firm*—Adduci, Mastriani, Schaumberg & Schill

[57] ABSTRACT

A catheter with an aorta-occluding balloon comprises a tube 1 extending between its L-shaped distal end 8 and its proximal end 9, and having a main lumen 2 formed centrally of the tube, a first and second subordinate lumens 3 and 4, both of them extending longitudinally through the tube's periphery, and a balloon 5 secured to and around the tube's distal end 8. The first lumen 3 has at its end near the proximal end 9 a connector 6 for receiving a balloon-expanding means, and the second lumen 4 also has at its end near the proximal end 9 a further connector 7 for receiving a solution-feeding means. The catheter is thus designed to occlude a calcified blood vessel so that its intima may not be injured, and a fluid such as a protective solution can be supplied to the cardiac muscle through the coronary artery.

8 Claims, 2 Drawing Sheets

CATHETER WITH AN AORTA-OCCLUDING BALLOON

BACKGROUND OF THE INVENTION

1. Field of the Invention

The present invention relates to a catheter with an aorta-occluding balloon, and more particularly to such a catheter as adapted for use for example in a surgical operation in which an aorta portion having an aneurism extending to an aortic arch is resected and replaced with a length of artificial blood vessel, or for use in the angiotomy in which the large blood vessels such as aorta or vena cava are subjected to surgical operation, or for use in the cardiotomy performed for surgical treatment of an acquired or congenital heart disease.

2. Prior Art

The science of cardiovascular surgery has recently made a marked advance so that nowadays the cardiotomy and angiotomy which are very difficult and has been regarded as almost impossible can often be performed. In a case wherein for example the aneurism in an aorta is surgically treated, a patient's death caused by the stopping of blood circulation must be avoided. Therefore, the operated vessel portion should be by-passed to maintain the blood flow through his or her whole body, for the purpose of life support. Such by-pass tubes are generally called the "blood-transporting tubes", and various types have been proposed (as disclosed for instance in the Japanese Patent Publication Hei. 2-39255).

Those prior art blood-transporting tubes are used when the large blood vessels are surgically treated not only in the cardiotomy but also in the implantation of artificial blood vessels. The former operation is for the congenital cardiopathy such as the valvular disease, or for the acquired heart diseases such as myocardial infarct and the ischemic cardiopathy which is typically a heart attack. The latter operation is conducted to resect and replace an aneurism portion of blood vessel with a length of artificial blood vessel. It is however to be noted that, when such a prior art blood-transporting tube is employed, the blood vessel portions adjacent to the operated region must be clamped by means of forceps or the like. If a blood vessel which has calcified due to arteriosclerosis or the like disease is clamped, then the intima of clamped portion will be injured. In another case wherein the aorta is clamped, the blood flow through the coronary artery will be stopped to unintentionally cause myocardial infarct or other heart disease.

The Japanese Patent Laying-Open Gazette Sho. 52-128681 discloses a proposal, which was made to resolve the above-described problems inherent in the prior art blood-transporting tubes. According to this proposal, a T-shaped catheter is provided which comprises balloons formed adjacent to the ends of thin lumens. The balloons occlude the body passage, for example a blood vessel, in such a state that it is possible to confine the stopping of the blood to the heart muscle to the small area where the by-pass is being made and for a short period of time. However, those balloons in the T-shaped catheter function in almost the same manner as forceps or clamps. This catheter can avoid the injury of the calcified blood vessels, though the other problem of the undesirable interception of blood flow to the coronary artery still remains unresolved, forcing the operation to be quickly finished in a short time.

SUMMARY OF THE INVENTION

An object of the present invention, which was made in view of the aforementioned problems, is therefore to provide a catheter comprising an aorta-occluding balloon and adapted to occlude the calcified blood vessel in such a state that the intima thereof will not be injured and further a fluid such as a protective solution can be supplied to the cardiac muscle through the coronary artery.

A catheter with an aorta-occluding balloon provided herein to achieve the object comprises a main lumen formed with a proximal end and a curved distal end of an L-shape, with the main lumen extending between the ends so as to bring them into fluid communication with one another, a balloon secured to and around the distal end, a first subordinate lumen extending along the main lumen and opening into the balloon, a connector disposed adjacent to the proximal end so as to receive a balloon-expanding means, with the first subordinate lumen being in fluid communication with the connector, a second subordinate lumen also extending along the main lumen and having an open end adjacent to the L-shaped distal end and opposite to the balloon, a further connector also disposed adjacent to the proximal end so as to receive a solution-feeding means, with the second subordinate lumen being in fluid communication with the further connector.

The open end, which defines a distal end of the second subordinate lumen and opens outwardly of the catheter, may preferably be located near an L-shaped corner of the distal end of the main lumen, with the L-shaped corner being located opposite to the balloon.

In use of the catheter, it will be inserted into an aorta "A" through a slit "D" opened through a wall of the aorta, as shown in FIG. 2. The main lumen will be set in place so that its open end 11 faces a distal or downstream portion "B" of the aorta, while the open end of the second subordinate lumen faces a proximal or upstream portion "C" of said aorta. The proximal end of the main lumen will be connected to a heart-lung machine or the like apparatus in such a state that the blood entering the main lumen is continuously discharged through its open end to flow into the aorta "A" and towards the downstream portion "B" thereof. Thereafter, the balloon-expanding means (not shown) will be connected to the connector so that the balloon is charged with a proper fluid through the first subordinate lumen. With the proper fluid being supplied in this way, the balloon will expand to closely contact the inner periphery of the aorta. The expanded balloon will tightly occlude the aorta so as to prevent the blood from moving towards the upstream portion "C" which will subsequently undergo a surgical operation. Because the coronary artery (not shown) feeding the oxygen and nutriment to the cardiac muscle branches away from the upstream portion "C" of aorta "A", a continued stoppage of blood flow thereto will cause the myocardinal infarct or other acute disease of the cardiac muscle. Therefore, a solution-feeding means (not shown) will be connected to the proximal end of the further connector so that the second subordinate lumen is used to allow the protective solution for cardiac muscle to flow through the coronary artery.

THE PREFERRED EMBODIMENTS

Figure 1:
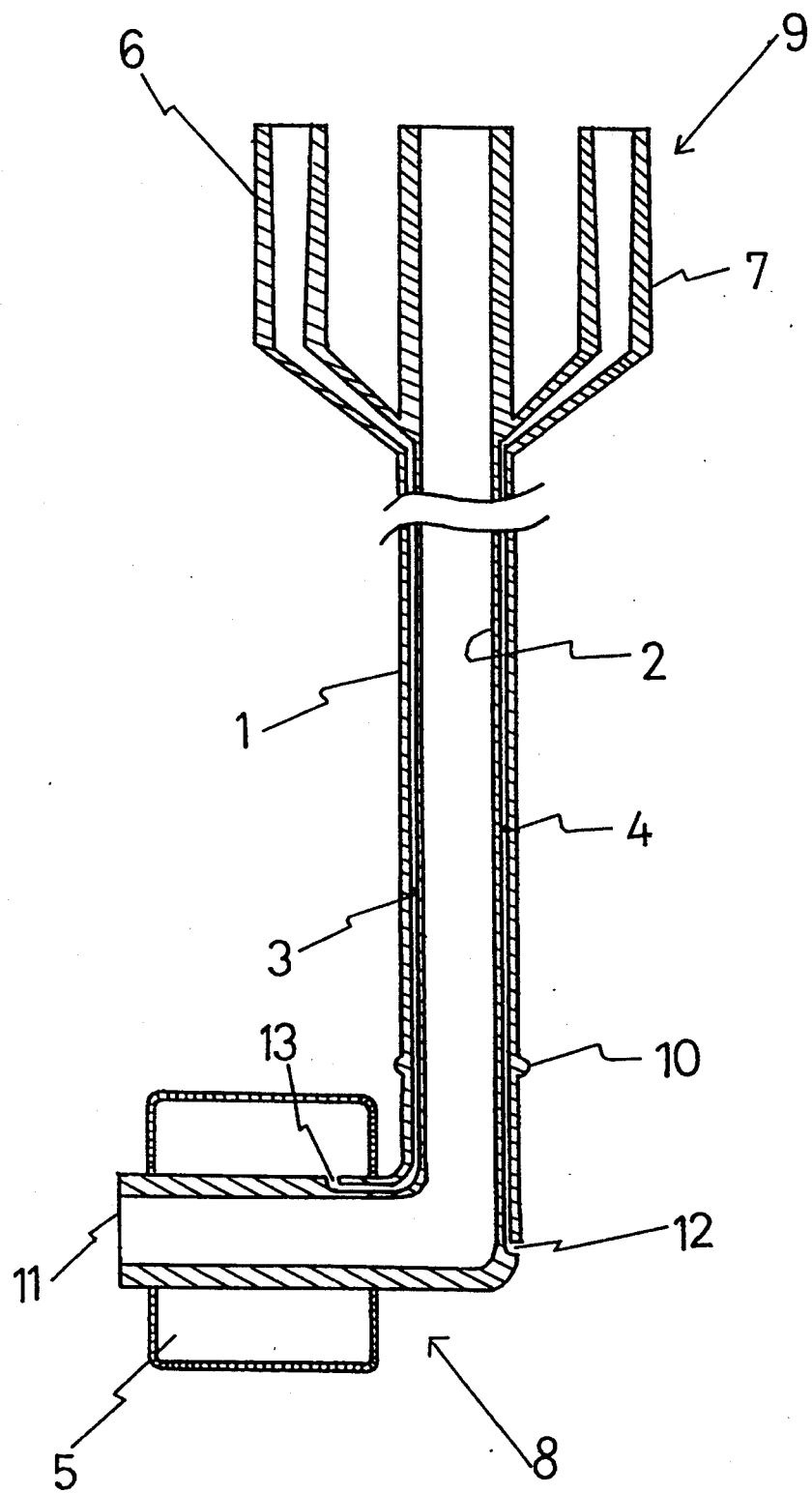
FIG. 1 is a cross-sectional view of a catheter which is provided in an embodiment, wherein an aorta-occluding balloon of the catheter is shown in its expanded state.
Figure 2:
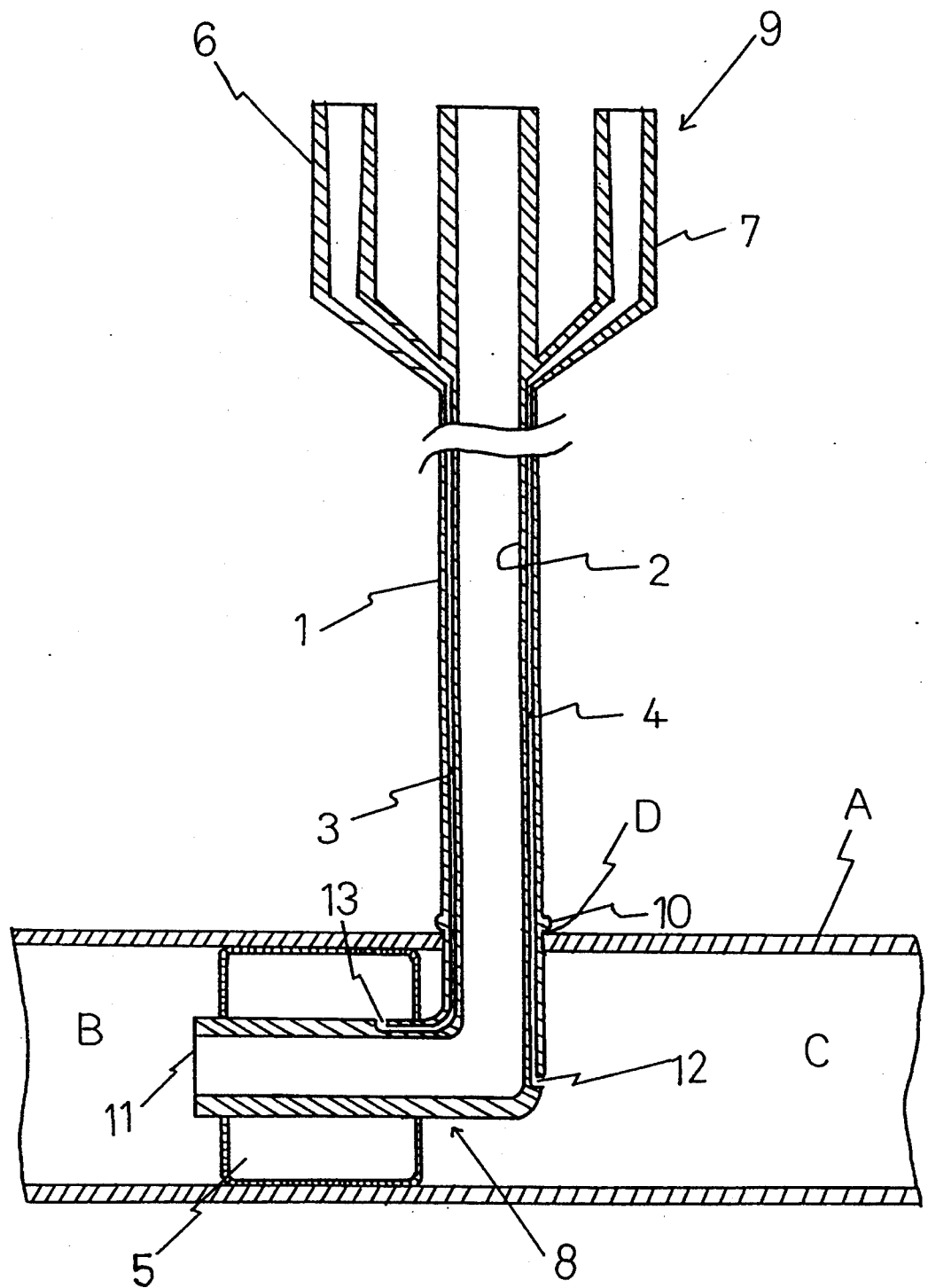
FIG. 2 is also a cross-sectional view of the catheter, with its distal end inclusive of the balloon being placed in an aorta.

An embodiment of the present invention will now be described referring to the drawings.

As shown in FIG. 1, a catheter with an aorta-occluding balloon comprises a tube 1. The tube 1 having a distal end 8 bent into an L-shape is composed of a main lumen 2, a first subordinate lumen 3 and a second subordinate lumen 4. The main lumen 2 extends through a central axial zone of the tube 1, whereas the subordinate lumens 3 and 4 extend along the main lumen and through a peripheral wall of the tube 1. The catheter comprises also a balloon 5 formed around the tube's distal end 8, in addition to a connector 6 for receiving a balloon-expanding means and a further connector 7 for a solution-feeding means. Those connectors 6 and 7 are formed integral with a proximal end 9 of the tube 1.

Such a composite tube 1 having the L-shaped distal end is made of a soft plastic such as a soft polyvinyl chloride, a polyurethane rubber or silicone rubber, and usually has a length of 250–300 mm and an outer diameter of 10–13 mm. The L-shaped distal end 8 is a section adapted for insertion into a blood vessel, with the section usually being 30–50 mm long from the axis to the tip end of the tube. The main lumen 2 penetrates the central region of the tube 1 and opens at the tip end thereof. The inner diameter of the main lumen 2 should be 7 mm or more, in consideration of the blood flow rate which may occasionally be set at 4–5 liters per minute. The outer diameter of the tube 1 primarily depends on the size of the main lumen 2, but is designed so small as not to have an excessively large slit "D" formed through the blood vessel wall.

As described above, the first and second subordinate lumens 3 and 4 extend through the peripheral wall of the tube 1 and along the main lumen 2. The first subordinate lumen 3 is a passageway for a fluid transported to and expanding the balloon disposed at the distal end 8. An open end 13 of the first subordinate lumen 3 is on the outer surface of the peripheral wall of the distal end 8 so as to be in communication with the interior of the balloon 5. The fluid expanding the balloon may be a compressed air, a salt solution or any other proper fluid. On the other hand, the second subordinate lumen 4 is another passageway for a nutritious solution or blood which may be selectively supplied to the occluded upstream portion "C" of the aorta. An open end 12 of the the second subordinate lumen 4 is disposed at the L-shaped distal end 8 and opposite to the balloon 5. Therefore, the second subordinate lumen 4 extends to and in fluid communication with the further connector 7, which connector is located beside the proximal end 9 so as to be connectable to the not shown solution-feeding means. Such an open end 12 of the lumen 4, which opens outwardly of the catheter, is desirably positioned in the proximity of a corner of the L-shaped portion of the catheter. Thus, the solution which may usually be a protective solution for the cardiac muscle can be fed from through the further connector 7 and the second subordinate lumen 4 and into the upstream portion "C" of the aorta. An example of such a protective solution is "GIK" which contains glucose and insulin in combination with a potassium compound. Those first and second subordinate lumens 3 and 4 may generally have an inner diameter of 0.3–1 mm, though not delimited thereto.

The balloon 5 secured to and formed around the distal end 8 of the tube 1 is made of a soft material, the typical examples thereof being a soft polyvinyl chloride resin and a silicone rubber. The diameter of the balloon expanded depends on the size and nature of a blood vessel to which the catheter need be applied, and may generally be 15–40 mm. The outer peripheral surface of the expanded balloon 5, which comes into a close contact with the inner peripheral surface of the blood vessel, must be designed as large as possible. It is therefore desirable that the outer surface extends substantially in parallel with the axis of the tube 1. Such a configuration will be effective to avoid the slippage of the balloon relative to the blood vessel, thus preventing the leakage of the blood. The connector 6 for the balloon-expanding means and the further connector 7 for receiving the solution-feeding means may usually be of such a shape that the tips of injectors are tightly connected to them. The reference numeral 10 denotes a flange or stopper formed on the tube 1, which flange hinders the tube's portion behind it from entering the blood vessel.

It will now be apparent that the catheter with the aorta-occluding balloon provided herein is beneficial to: (1) the surgical operation of aorta in which an aneurismal portion extending to aortic arch is resected and replaced with a length of artificial blood vessel; to the angiotomy for surgical treatment of large blood vessels such as the aorta; and also to the cardiotomy for surgical treatment of an acquired or congenital heart disease. When a calcified vessel is occluded, the catheter's balloon will so gently press the blood vessel intima surface that it will be protected from a damage which the aorta-occluding forceps has inevitably caused. The catheter, which can supply the coronary artery with a protective solution or blood for cardiac muscle is beneficial also to: (2) the protection of any operated large vessel from the myocardial infarct or other harmful effects which have often brought about by the prior art surgical operation.

In addition to the surgical operation of an aorta, the catheter with the aorta-occluding balloon provided herein may also be used in the other surgical operations such as the transportation of a heart.

What is claimed is:

1. A catheter with an aorta-occluding balloon, the balloon having an inner surface and an outer surface, the catheter comprising:

a main lumen formed with a proximal end and an L-shaped distal end;

the main lumen extending between the ends so as to bring the ends into fluid communication with one another;

the balloon being secured to and around the distal end;

a first subordinate lumen extending along the main lumen and opening into the balloon;

a connector disposed adjacent to the proximal end so as to receive a balloon-expanding means for expanding said balloon, with the first subordinate lumen being in fluid communication with the connector;

a second subordinate lumen also extending along the main lumen and having an end open outwardly of the catheter adjacent to the L-shaped distal end and opposite to the balloon;

a further connector also disposed adjacent to the proximal end so as to receive a solution-feeding means, with the second subordinate lumen being in fluid communication with the further connector, said catheter being insertable into an aorta, said balloon-expanding means expanding said balloon so as to place said outer surface in contact with the aorta, said outer surface extending substantially parallel with the L-shaped distal end.

2. A catheter as defined in claim 1, wherein the distal open end of the second subordinate lumen opens outwardly of the catheter, at or near an L-shaped corner of the distal end of the main lumen, with the L-shaped corner being disposed opposite to the balloon.

3. A catheter as defined in claim 1, wherein the main lumen, the first subordinate lumen and the second subordinate lumen are formed side by side and integral with each other so as to form an integral tube.

4. A catheter as defined in claim 2, wherein the main lumen, the first subordinate lumen and the second subordinate lumen are formed side by side and integral with each other to form an integral tube.

5. A catheter with an aorta-occluding balloon, the balloon having an inner surface and an outer surface, the catheter comprising:

a main lumen formed with a proximal end and an L-shaped distal end;

the main lumen extending between the ends so as to bring the ends into fluid communication with one another;

the balloon being secured to and around the distal end;

a first subordinate lumen extending along the main lumen and opening into the balloon;

a connector disposed adjacent to the proximal end so as to receive a balloon-expanding means for expanding said balloon, with the first subordinate lumen being in fluid communication with the connector;

a second subordinate lumen also extending along the main lumen and having an end open outwardly of the catheter adjacent to the L-shaped distal end and opposite to the balloon;

a further connector also disposed adjacent to the proximal end so as to receive a solution-feeding means, with the second subordinate lumen being in fluid communication with the further connector, said catheter being insertable into an aorta, said balloon-expanding means expanding said balloon so as to place said outer surface in contact with the aorta, said outer surface extending substantially parallel with the L-shaped distal end; and flange means provided on an outer surface of the main lumen for preventing insertion of the main lumen into said aorta more than a predetermined distance, said predetermined distance extending from the L-shaped distal end to said flange means.

6. A catheter as defined in claim 5, wherein the distal open end of the second subordinate lumen opens outwardly of the catheter, at or near an L-shaped corner of the distal end of the main lumen, with the L-shaped corner being disposed opposite to the balloon.

7. A catheter as defined in claim 5, wherein the main lumen, the first subordinate lumen and the second subordinate lumen are formed side by side and integral with each other so as to form an integral tube.

8. A catheter as defined in claim 6, wherein the main lumen, the first subordinate lumen and the second subordinate lumen are formed side by side and integral with each other to form an integral tube.

* * * * *